United States Patent [19]

Ahr et al.

[11] Patent Number: 5,763,044
[45] Date of Patent: *Jun. 9, 1998

[54] FLUID PERVIOUS, DISPERSIBLE, AND FLUSHABLE WEBS HAVING IMPROVED FUNCTIONAL SURFACE

[75] Inventors: Nicholas Albert Ahr, Cincinnati; Raymond John Dirk, Cleves, both of Ohio

[73] Assignee: The Procter & Gamble Company, Cincinnati, Ohio

[*] Notice: The term of this patent shall not extend beyond the expiration date of Pat. No. 5,722,966.

[21] Appl. No.: 561,721

[22] Filed: Nov. 22, 1995

[51] Int. Cl.$^6$ .............................. A61F 13/15; B32B 3/16
[52] U.S. Cl. .................. 428/131; 428/119; 428/85; 428/913; 428/338; 428/220; 604/383; 604/378; 604/365; 604/367; 604/375; 442/62; 442/153
[58] Field of Search ........................ 428/131, 119, 428/85, 913, 338, 220; 604/383, 378, 365, 367, 375; 442/62, 153

[56] References Cited

U.S. PATENT DOCUMENTS

| | | | |
|---|---|---|---|
| 3,078,849 | 2/1963 | Morse | 128/290 |
| 3,141,051 | 7/1964 | Takai | 264/219 |
| 3,407,814 | 10/1968 | George et al. | 128/290 |
| 3,510,587 | 5/1970 | Marder | 128/284 |
| 3,542,028 | 11/1970 | Beebe | 128/290 |
| 3,561,447 | 2/1971 | Alexander | 128/290 |
| 3,575,173 | 4/1971 | Loyer | 604/387 |
| 3,636,952 | 1/1972 | George | 128/287 |
| 3,665,923 | 5/1972 | Champaigne | 128/290 W |
| 3,683,919 | 8/1972 | Ells | 128/290 W |
| 3,696,183 | 10/1972 | Steel et al. | 264/164 |
| 3,950,578 | 4/1976 | Laumann | 427/378 |
| 3,965,906 | 6/1976 | Karami | 128/287 |
| 3,967,623 | 7/1976 | Butterworth et al. | 128/287 |
| 3,994,771 | 11/1976 | Morgan, Jr. et al. | 162/113 |
| 4,102,737 | 7/1978 | Morton | 162/113 |
| 4,141,772 | 2/1979 | Buell | 156/227 |
| 4,311,745 | 1/1982 | Civardi | 428/91 |
| 4,342,314 | 8/1982 | Radel et al. | 128/287 |
| 4,391,878 | 7/1983 | Drach | 428/479.6 |
| 4,508,256 | 4/1985 | Radel et al. | 228/152 |
| 4,585,449 | 4/1986 | Karami | 604/378 |
| 4,628,857 | 12/1986 | Coningsby | 118/406 |

(List continued on next page.)

FOREIGN PATENT DOCUMENTS

| | | | |
|---|---|---|---|
| 07-003699 | 1/1995 | Japan | D21H 27/00 |
| 07-3699 | 1/1995 | Japan. | |
| 282447 | 5/1928 | United Kingdom. | |
| WO 93/19715 | 10/1993 | WIPO. | |
| WO 95/03361 | 2/1995 | WIPO. | |
| WO 95/16474 | 6/1995 | WIPO. | |
| WO 95/18191 | 7/1995 | WIPO. | |
| WO 95/30049 | 11/1995 | WIPO. | |

*Primary Examiner*—William Watkins
*Attorney, Agent, or Firm*—William Scott Andes; Roddy M. Bullock; E. Kelly Linman

[57] ABSTRACT

The present invention relates to fluid pervious, dispersible, and flushable webs particularly suited for use in a disposable absorbent article, such as a diaper, sanitary napkin, panty liner, incontinence pad, or the like. The present invention further relates to such webs which also include an improved, functional textured surface so as to be suitable for use as a topsheet on such a disposable absorbent article.

The present invention provides a fluid pervious web which disperses into fragments which are readily flushable in a normal toilet. The web preferably comprises a wetlaid apertured tissue having a temporary wet strength resin incorporated therein. The web preferably further includes a plurality of individual fibrils on a body-facing surface thereof, so as to provide a clean and dry tactile impression in use. The fibrils serve to separate the wearer's skin from the underlying tissue substrate in use. In a preferred embodiment, the web substrate is hydrophilic in nature while the fibrils themselves are hydrophobic in nature, so as to provide enhanced dryness at the uppermost surface while promoting rapid acquisition properties.

20 Claims, 3 Drawing Sheets

U.S. PATENT DOCUMENTS

| | | | |
|---|---|---|---|
| 4,637,859 | 1/1987 | Trokhan | 162/109 |
| 4,655,757 | 4/1987 | McFarland et al. | 604/366 |
| 4,725,473 | 2/1988 | Van Gompel et al. | 428/156 |
| 4,741,941 | 5/1988 | Englebert et al. | 428/71 |
| 4,743,483 | 5/1988 | Shimizu et al. | 428/89 |
| 4,878,825 | 11/1989 | Mullane et al. | 425/290 |
| 4,940,513 | 7/1990 | Spendel | 162/112 |
| 5,015,245 | 5/1991 | Noda | 604/367 |
| 5,026,363 | 6/1991 | Pratt | 604/385.1 |
| 5,058,247 | 10/1991 | Thomas et al. | 24/448 |
| 5,102,597 | 4/1992 | Roe et al. | 264/126 |
| 5,116,563 | 5/1992 | Thomas et al. | 264/167 |
| 5,124,111 | 6/1992 | Keller et al. | 264/555 |
| 5,128,082 | 7/1992 | Makoui | 264/112 |
| 5,158,819 | 10/1992 | Goodman, Jr. et al. | 428/131 |
| 5,180,534 | 1/1993 | Thomas et al. | 264/145 |
| 5,190,533 | 3/1993 | Blackburn | 604/367 |
| 5,207,662 | 5/1993 | James | 604/385.2 |
| 5,217,576 | 6/1993 | Van Phan | 162/158 |
| 5,221,276 | 6/1993 | Battrell | 604/391 |
| 5,229,186 | 7/1993 | Tribble et al. | 428/156 |
| 5,230,851 | 7/1993 | Thomas | 264/145 |
| 5,300,358 | 4/1994 | Evers | 428/286 |
| 5,318,741 | 6/1994 | Thomas | 264/145 |
| 5,384,189 | 1/1995 | Kuroda et al. | 428/288 |
| 5,405,342 | 4/1995 | Roessler et al. | 604/364 |
| 5,415,643 | 5/1995 | Kolb | 604/367 |
| 5,417,679 | 5/1995 | Toms et al. | 604/370 |
| 5,431,643 | 7/1995 | Ouellette et al. | 604/385.1 |
| 5,454,801 | 10/1995 | Lauritzen | 604/378 |
| 5,466,337 | 11/1995 | Darlington et al. | 162/164.3 |

FLUID PERVIOUS, DISPERSIBLE, AND FLUSHABLE WEBS HAVING IMPROVED FUNCTIONAL SURFACE

FIELD OF THE INVENTION

The present invention relates to fluid pervious, dispersible, and flushable webs particularly suited for use in a disposable absorbent article, such as a diaper, sanitary napkin, panty liner, incontinence pad, or the like. The present invention further relates to such webs which also include an improved, functional textured surface so as to be suitable for use as a topsheet on such a disposable absorbent article.

BACKGROUND OF THE INVENTION

All manner and variety of absorbent articles configured for the absorption of bodily fluids are, of course, well known. Current types of absorbent articles include sanitary napkins, pantiliners, disposable diapers, and incontinent articles. A long felt need has existed for more convenient and discrete disposal methods for such absorbent articles, particularly for sanitary napkins and the like. One method that would provide such improved convenience and discretion would be the use of a conventional toilet for such disposal. However, there is a substantial risk of disposal problems, such as clogging, if commercially available sanitary napkins are disposed of by flushing them down a conventional toilet.

In order to provide absorbent articles which are disposable in such fashion, it is of course necessary to provide them with individual components which readily disintegrate when in contact with water. The desirability for absorbent articles and components thereof which disintegrate in the course of flushing down a conventional toilet of necessity places some limitations upon the choice of component materials. For example, topsheet structures formed from apertured plastic films have found wide acceptance in such articles. Such materials, however, as currently commercially available maintain their integrity in contact with fluids and do not break apart during the course of being subjected to flushing down a toilet.

A number of cellulosic fibrous sheet materials in the form of paper or tissue products have been developed which provide a soft tactile impression, as well as good strength and integrity properties. Exemplary of such materials are those described in greater detail in U.S. Pat. Nos. 5,245,025, issued Sep. 14, 1993 to Trokhan et al., 4,637,859, issued Jan. 20, 1987 to Trokhan, and 4,529,480, issued Jul. 16, 1985 to Trokhan, the disclosures of each of which are hereby incorporated herein by reference. Such materials rely largely upon hydrogen bonding between the individual cellulosic fibers to provide integrity in use, and thus the potential for such materials to be broken down by contact with water.

While such materials have been employed to great advantage in a wide variety of contexts, including as components of absorbent articles, their usefulness as a topsheet material is less than optimal due to their predominantly hydrophilic nature. While hydrophilicity provides desirable acquisition characteristics, it is frequently accompanied by a "wet" or moist tactile impression following contact with a fluid, as the cellulosic materials themselves are not only hydrophilic but absorbent as well.

Accordingly, it would be desirable to provide fluid pervious webs which not only disintegrate in contact with water to provide for flushability, but also provide for desirable acquisition and dryness properties when utilized as a topsheet material in an absorbent article.

SUMMARY OF THE INVENTION

The present invention provides a fluid pervious web which disperses into fragments which are readily flushable in a normal toilet. The web preferably comprises a wetlaid apertured tissue having a temporary wet strength resin incorporated therein. The web preferably further includes a plurality of individual fibrils on a body-facing surface thereof, so as to provide a clean and dry tactile impression in use. The fibrils serve to separate the wearer's skin from the underlying tissue substrate in use. In a preferred embodiment, the web substrate is hydrophilic in nature while the fibrils themselves are hydrophobic in nature, so as to provide enhanced dryness at the uppermost surface while promoting rapid acquisition properties.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

General Description of the Representative Absorbent Article

Figure 1:
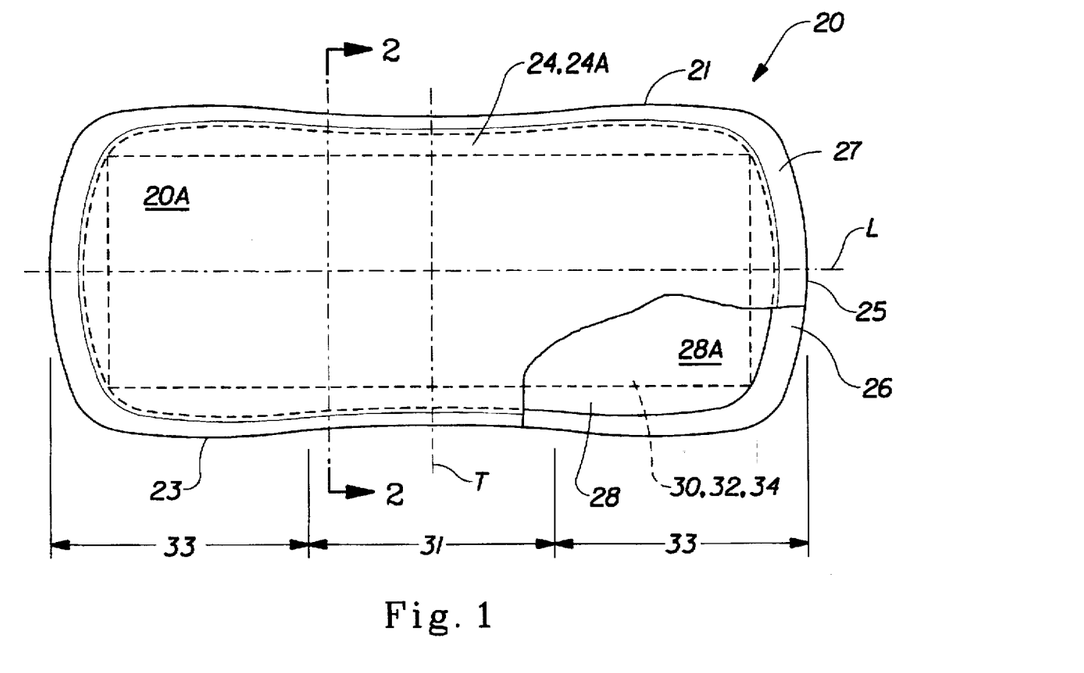
FIG. 1 is a top plan view, partially sectioned, of a preferred absorbent article configuration in the form of a sanitary napkin incorporating a fluid pervious web according to the present invention.

FIG. 1 is a plan view of the representative absorbent article, sanitary napkin 20, in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a liquid impervious backsheet 26 joined with the topsheet 24, an absorbent core 28 positioned between the topsheet 24 and the backsheet 26, and attachment means 30 for releasably attaching the sanitary napkin 20 to a wearer's undergarment.

The sanitary napkin 20 has two surfaces, a body-contacting surface or "body surface" 20A and a garment surface 20B. In a similar manner each component comprising the sanitary napkin 20 may have a body surface designated by the reference number for the component with an appended A and a garment surface designated by the reference number for the component and an appended B. The sanitary napkin 20 is shown in FIG. 1 as viewed from its body surface. The body surface 20A is intended to be worn adjacent to the body of the wearer while the garment surface 20B is on the opposite side and is intended to be placed adjacent to the wearer's undergarments when the sanitary napkin 20 is worn. The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 also shows that the sanitary napkin 20 has a periphery 21 which is defined by the outer edges of the sanitary napkin 20 in which the longitudinal edges are designated 23 and the end edges are designated 25. A central region 31 is disposed between two end regions 33. The end regions 33 extend longitudinally outwardly from the edges of the central region 31 about 12% to about 33% of the length of the sanitary napkin. A detailed description of a sanitary napkin having a central region 31 and the two end regions 33 is contained in U.S. Pat. No. 4,690,680, issued to Higgins on Sep. 1, 1987.

Figure 2:
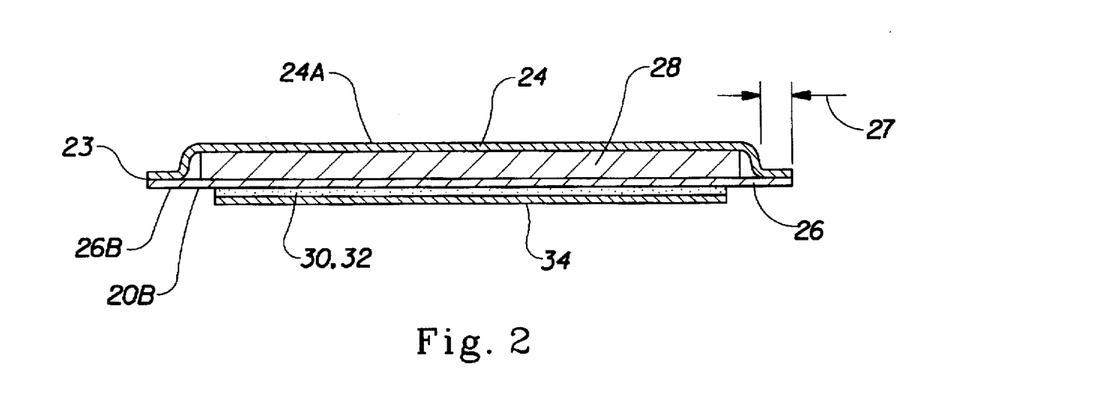
FIG. 2 is an enlarged cross-sectional view of the absorbent article of FIG. 1 taken along line 2—2.

While the topsheet, the backsheet, and the absorbent core may be assembled in a variety of well known configurations (including so called "tube" products or side flap products), preferred sanitary napkin configurations are described generally in U.S. Pat. No. 4,950,264, issued to Osborn on Aug. 21, 1990; U.S. Pat. No. 4,425,130, issued to Desmarais on Jan. 10, 1984; U.S. Pat. No. 4,321,924, issued to Ahr on Mar. 30, 1982; and U.S. Pat. No. 4,589,876, issued to Van Tilburg on Aug. 18, 1987. The disclosures of each of these patents are hereby incorporated herein by reference. FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form at least a portion of the periphery 21. FIG. 2 depicts in greater detail the relationship between the various components of the sanitary napkin view from a cross-sectional perspective.

The representative absorbent article, sanitary napkin 20, is described in greater detail in commonly-assigned, co-pending U.S. patent application Ser. No. 08/561,989, pending Attorney's Docket No. 5877, filed Nov. 22, 1995 in the names of Christon and Ahr, entitled "Water Dispersible and Flushable Absorbent Article", the disclosure of which is hereby incorporated herein by reference. Suitable test and analytical methods for measuring various functional and characteristic attributes of such absorbent articles are also described in such application.

The Topsheet

In accordance with the present invention, the topsheet 24 of sanitary napkin 20 is compliant, soft feeling, and non-irritating to the wearer's skin. Further, the topsheet 24 is liquid pervious permitting liquids (e.g., menses and/or urine) to readily penetrate through its thickness. The topsheet should also be readily dispersible under the mild agitation conditions encountered when a conventional toilet is flushed. A suitable topsheet 24 may be manufactured from a wide range of materials such as air laid, wet laid, or carded nonwoven materials. Suitable materials can be comprised of natural fibers (e.g., wood or cotton fibers), synthetic fibers (e.g., polymeric fibers such as polyester, polypropylene, or polyethylene fibers) or from a combination of natural and synthetic fibers.

Figures 4, 8:
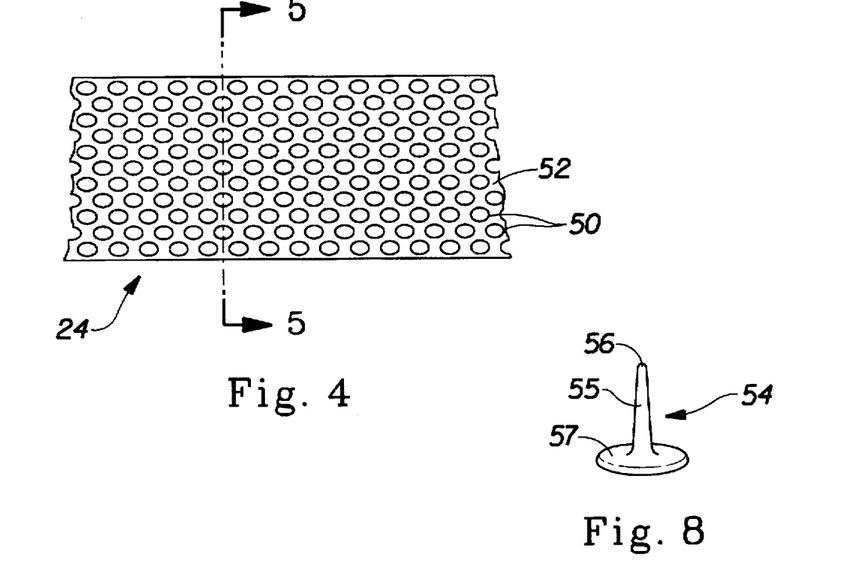
FIG. 4 is a plan view of a fluid pervious web according to the present invention.
FIG. 8 is a greatly enlarged, perspective illustration of an individual fibril 54 such as depicted in FIGS. 5–7.
Figure 5:
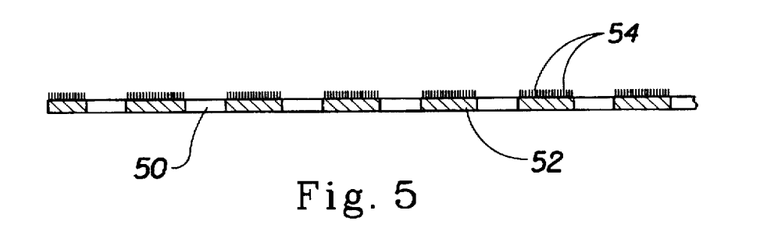
FIG. 5 is an enlarged cross-sectional view taken along line 5—5 of FIG. 4.

A preferred topsheet 24 comprises a wetlaid apertured tissue having a temporary wet strength resin incorporated therein as a substrate. A portion of such topsheet 26 is shown in FIGS. 4 and 5. As is shown in FIGS. 4 and 5, the wet laid tissue that comprises the preferred topsheet 26 comprises a wetlaid fibrous assembly 52 having a multiplicity of apertures 50 therethrough. While a preferred fiber furnish for this tissue comprises wood fibers, preferably about 90 percent Eucalyptus fibers and about 10% Northern Sulfite Kraft fibers, other fibrous materials, including but not limited to natural fibers (e.g., other types of wood fibers or cotton fibers), synthetic fibers (e.g., polymeric fibers such as polyester, polypropylene, or polyethylene fibers) or a combination of natural and synthetic fibers are also suitable as long as the fibers are, or can be treated to become, hydrophilic. Such a wetlaid apertured tissue can be produced on a paper machine according to the method described in U.S. Pat. No. 3,881,987, issued to Benz on May 6, 1975. Preferably, the drainage member described in the aforementioned Benz patent should comprise the foraminous members described in U.S. Pat. No. 4,514,345, issued to Johnson, et al. on Apr. 30, 1985. The disclosure of each of these patents is incorporated herein by reference. The embryonic fibrous webs as would be produced as described above can be further dried using any convenient drying means as would be known to those skilled in the paper making art. For example, press felts, thermal hoods, infra-red radiation, blow-through dryers and Yankee drying drums, either used alone or in combination. A particularly preferred drying method uses a press felt and a Yankee drying drum in sequence.

The use of such a method can provide wetlaid fibrous assemblies having a range of aperture densities and percent open area. As used herein, the term "aperture density" is intended to mean the number of apertures per square inch of fibrous assembly surface and the term "percent open area" is defined as that portion of the fibrous assembly surface that is not occupied by fibers expressed as a percentage. Preferably the aperture density is between about 9 apertures per square inch (1 aperture per square centimeter) and about 400 apertures per square inch (62 apertures per square centimeter). More preferably, the aperture density is between about 20 apertures per square inch (3 apertures per square centimeter) and about 111 apertures per square inch (17 apertures per square centimeter). The preferred apertured wetlaid fibrous assemblies of the present invention preferably have a percent open area between about 20 percent and about 50 percent. More preferably, the percent open area is between about 30 percent and about 40 percent. A particularly preferred wetlaid fibrous assembly has an aperture density of about 81 apertures per square inch (6 apertures per square centimeter) with about 36 percent open area.

The tissue furnish further comprises a temporary wet strength resin. Such a temporary wet strength resin helps the topsheet 24 maintain its mechanical integrity during use of the sanitary napkin 20 yet does not interfere with the dispersibility of the topsheet when the used sanitary napkin 20 is flushed. Suitable temporary wet strength resin are the glyoxalated polyacrylamide resins available from Cytec Industries Inc. of Stanford, Conn. under the designation Parez™. Particularly preferred is Parez™ 631 NC. When Parez™ 631 NC is used at a level between about 0.5% and about 1.0% in the wet laid apertured tissue, the topsheet 24 has a satisfactory balance of mechanical integrity during use and dispersibility during disposal.

This preferred tissue is further provided with a multiplicity of fibrils 54 or "hairs" on the non-apertured portion of its body facing surface. These fibrils 54 improve the surface wetness characteristics of the topsheet 24 by separating the wearer's body from any bodily fluids that may remain on the cellulosic body side surface of the topsheet 24A. Similarly, this separation from a wearer's body improves the acquisition rate for bodily fluids. The fibrils 54 also provide the body surface 24A with a pleasant, velour-like tactile feel. At the same time, the fibrils must be constructed and applied such that the flushability and dispersibility of the substrate material is substantially unimpaired in the finished topsheet.

The fibrils 54 preferably comprise a water resistant resinous material such as a hot melt resin blend, which is commercially available from Century International of Columbus, Ohio under the trade designation CA-105. The fibril density can vary between about 500 fibrils per square inch (77 fibrils per square centimeter) to about 11,000 fibrils per square inch (1700 fibrils per square centimeter). Preferably, the fibril density is between about 3000 fibrils per square inch (450 fibrils per square centimeter) and about 5000 fibrils per square inch (775 fibrils per square centimeter). Fibril length can vary between about 0.003 inches (0.07 mm) to about 0.04 inches (1.0 mm). Preferably, the fibril length is between about 0.004 inches (0.1 mm) and about 0.01 inch (0.3 mm). The Applicants have found that choice of fibril length and fibril density allows the rewet characteristics, the acquisition characteristics and the tactile feel to be varied to achieve a desired balance of these characteristics.

Preferably, such fibrils are formed from a material which is generally hydrophobic in nature, or from a material which is rendered hydrophobic by known methods. This provides a wearer-contacting surface (the ends of the fibrils) which tends to repel fluids and provide a "dry" tactile impression, while the remainder of the web retains its hydrophilic characteristics to provide for enhanced acquisition properties. Such fibrils are described in greater detail in commonly-assigned, co-pending U.S. patent application Ser No. 08/494,273, ABN filed Jun. 23, 1995 in the names of Ahr and Thomas, entitled "Absorbent Device with Improved Functional Surface", the disclosure of which is hereby incorporated herein by reference.

Alternatively, a wetlaid apertured tissue produced according to the aforementioned U.S. Pat. No. 3,881,987 on a drainage member as described in the aforementioned U.S. Pat. No. 4,514,345 and having a wet strength resin incorporated therein may further comprise a garment surface 24B. The body surface 24A and the garment surface 24B are separated from one another by an intermediate portion. The wetlaid apertured tissue is treated to form a web such that the body surface of the web provides a structure which exhibits a surface energy less than the surface energy of the intermediate portion. In a preferred embodiment, the treated web exhibits a plurality of regions of comparatively low surface energy which define surface energy gradients where they interface with higher surface energy web surfaces. For example, a silicone resin having a low surface energy can be applied to portions of the body surface 24A providing such regions of comparatively low surface energy. Webs having such surface energy gradients are fully described in U.S. patent application Ser. No. 08/442,935, ABN filed on May 31, 1995 in the name of Ouellette, et al. the disclosure of which is incorporated herein by reference.

In a preferred embodiment of the present invention, at least portions of the body surface 24A of the topsheet 24 are hydrophilic so as to help liquid to transfer through the topsheet faster than if the body surface was not hydrophilic. Such a hydrophilic surface helps to diminish the likelihood that bodily fluids will flow off the topsheet rather than flowing into and being absorbed by the absorbent core. In a preferred embodiment, surfactant is applied to the body surface 24A of the topsheet 24 (e. g. by extrusion coating or spraying) before the fibrils are printed thereon. Alternatively, the body surface of the topsheet can be made hydrophilic by treating it with a surfactant such as is described in the above referenced U.S. Pat. No. 4,950,254, the disclosure of which is incorporated herein by reference.

Figure 6:
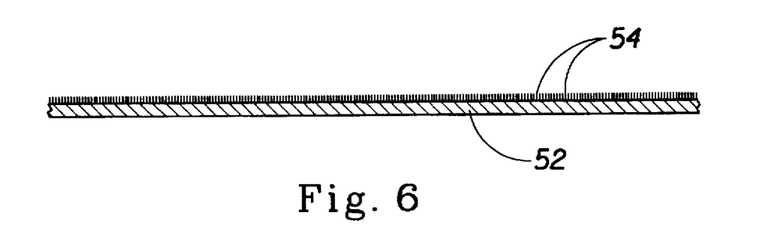
FIG. 6 is an enlarged cross-sectional view similar to that of FIG. 5 but of an alternative web configuration.
Figure 7:
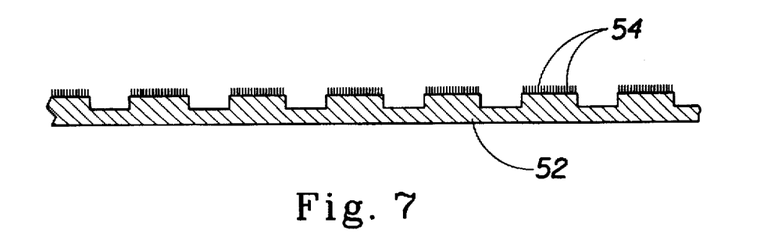
FIG. 7 is an enlarged cross-sectional view similar to that of FIG. 5 but of a further alternative web configuration.

FIGS. 6 and 7 depict alternative web structures according to the present invention. As depicted in FIG. 6, the fibrous assembly 52 does not include discrete apertures such as apertures 50 depicted in FIGS. 4 and 5. However, in order to maintain fluid transmission capabilities sufficient to enable their use in absorbent articles, such webs include sufficient inherent porosity. As with the web of FIGS. 4 and 5, the fibrils 54 are topographically printed upon the uppermost surface of the web rather than only upon the surface areas between apertures. Alternatively, if desired, the area provided with fibrils 54 may be of any desired shape, pattern, or coverage area and of either uniform or non-uniform density.

FIG. 7 depicts another embodiment of a cellulosic fibrous structure 52 according to the present invention. As shown in FIG. 7, the web includes regions of various caliper or topography. As with the web of FIG. 6, the web lacks discrete apertures but is provided with sufficient inherent porosity to maintain its functionality when included in a disposable absorbent article. As with the webs of FIGS. 4–6, the fibrils 54 are topographically printed upon the uppermost surface of the web rather than the entire upwardly-facing web surface.

With any webs of varying topography, it is to be understood that upon the application of sufficient compressive forces during the application of the fibrils 54, it may indeed be possible to apply fibrils to the entire upwardly-facing web surface due to the web being compressed to a uniform caliper and topography during the printing process.

A wide variety of cellulosic fibrous webs may be utilized as substrate materials in accordance with the present invention. A more detailed description of such webs, as well as methods and apparatus for forming them, may be found in the above-referenced and incorporated U.S. Pat. Nos. 4,529,480, 4,637,859, and 5,245,025. Other woven and nonwoven materials may also be utilized, including those recited above.

FIG. 8 depicts in much greater detail the physical structure of a typical fibril 54 such as depicted in FIGS. 5–9. Fibril 54 preferably comprises a shaft portion 55 which extends from a base 57 to a tip 56. In formation, the resin material is deposited as base 57 and drawn upward to form shaft 55. The resin material abruptly separates from the resin remaining on the screen roll 110, forming tip 56, which is preferably slightly rounded. Fibrils are preferably constructed and arranged such that their respective bases 57 are spaced at least slightly apart, such that the underlying substrate therebetween is at least slightly exposed both for acquisition and flushability purposes. In addition, the number and size of the fibrils must not be so great as to likewise impair the flushability and dispersibility of the topsheet.

The resin material utilized to form the fibrils preferably cures or hardens quickly after the fibril has been formed to the desired height and/or configuration. In this fashion, the fibril is "locked in" before the resin can begin to collapse back downward toward the base 57 and the fibril loses its shape. This relatively short cure time, or "open time", is also conducive to comparatively higher web speeds as it ensures the fibers are cured before subsequent web handling operations are undertaken.

If desired, the masking capabilities of the topsheet 24 can be enhanced by the addition of a dye or filler to the resinous material from which the fibrils 54 are made. Suitable masking agents include titanium dioxide and calcium carbonate. The fibrils 54 themselves, as well as the fillers aid in the masking of bodily fluids absorbed by the topsheet and the underlying absorbent core. The masking agent provides a clean and dry appearance by providing additional opacity to the topsheet as a whole, and particularly the upper surface thereof.

Fibrils 54 preferably have sufficient resilience by virtue of material properties, length, and thickness so as to be at least somewhat resistant to deflection toward the web surface when contacted by the wearer in use. If the fibrils collapse too readily, the effect of separation between the wearer and the fibrous hydrophilic substrate is diminished and increasingly "wet" tactile impression may be encountered. Collapsed fibrils if too great in number may also prove to impair fluid acquisition by blocking apertures or pores, in the substrate.

Fibrils 54 extend generally outwardly from the wearer-facing surface of the topsheet 24, as depicted generally in FIGS. 5–7. In a preferred configuration, a majority of the fibrils extend generally perpendicularly outwardly from the surface of the web, although at least some of the fibrils may extend outwardly at various angles.

The Process

The preferred method for applying the resinous material is by a rotary screen printing method. It is to be understood, however, that other methods of printing or spraying such resinous projections are contemplated by the present invention. Such methods include spiral spraying, mist spraying, or line spraying, gravure printing, and flexographic printing. Rotary screen printing is the most preferred because the method is capable of producing the sizes and densities of fibrils desired and can also be performed at high web line speeds.

Figure 3:
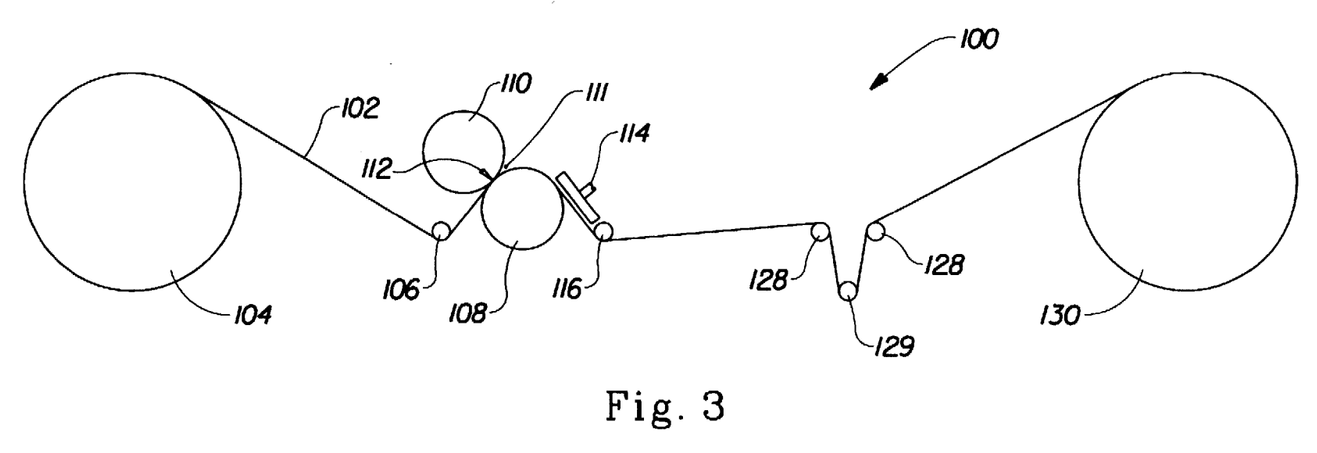
FIG. 3 is a schematic diagram of an apparatus suitable for forming the surface features of fluid pervious webs according to the present invention.

Referring to FIG. 3, which illustrates a suitable resin application apparatus 100, the process for producing a liquid impermeable and flushable web comprises the following steps. The substrate 102, having a mutually opposed first side and second side, is unwound from a parent roll 104. The substrate 102 is fed to a printing station 105 comprising a backing roll 108, a print roll 110, and a feed roll 106. The backing roll 108 is juxtaposed with the printing roll 110 to form a nip therebetween. The printing roll 110 has a plurality of cells disposed about its periphery. In a preferred embodiment, the backing roll 108 comprises a backing roll rotatable about its longitudinal axis. Resinous material is delivered to the interior of the print roll 110 by a delivery mechanism (not shown) such as those well known in the art.

Tension control devices and tracking devices (not shown) well known in the art may also be used in this process, if such devices are necessary to insure an even coating of the resinous material across the entire transverse width of the substrate 102.

The resinous material is provided to the print roll 110 in a liquid state. If the resinous material is in a solid state at room temperature, it may be heated to a temperature above its melting point. Alternatively, resinous materials in a liquid state at room temperature may be utilized. For example, prepolymers comprising chemically reactive end groups may be utilized. In this case, after depositing the resinous material onto and into the substrate 102, a subsequent curing step is necessary to convert a liquid prepolymer into a solid state.

In the preferred embodiment of the process, the resinous material is heated to at least its melting point, causing the resinous material to be flowable.

The substrate 102 is transported, at a transport velocity, relative to the printing roll 110 and the backing roll 108, through the nip defined by the printing roll 110 and the backing roll 108. The flowable resinous material is disposed in the cells of the printing roll 110. The substrate 102 is transported through the nip in contacting relation with the cells of the printing roll 110. The printing roll 110 rotates about its longitudinal axis at a peripheral velocity, thereby applying the flowable resinous material from the cells of the printing roll 110 onto the substrate 102. Preferably, the coating weight of the resinous material 200 on the substrate 102 is between about 0.005 grams per square inch and about 0.075 grams per square inch.

Referring again to FIG. 3, the web velocity and the tangential velocity of the screen roll 110 are substantially the same. This means that the CA-105 resin is printed on the web 102 rather than being wiped across the web surface. By control of the screen pattern on the screen roll 110 and of rheology of the CA-105 when it is in its melted state, the CA-105 is printed as the fibrils 54 described above. The holes in the screen are small enough and the resinous material is of sufficient viscosity that the resinous material will not flow through the holes in the screen on its own. The doctor blade forces the resinous material to fill up the screen holes such that a meniscus of material hangs down from the screen toward the backing roll. As the screen roll and backing roll rotate, the screen contacts the substrate at the point of the backing roll and the meniscus of resinous material transfers from the screen holes onto the substrate. As the screen and web separate, the attraction or adhesion of the resin material for itself and for the screen surface cause a portion of the resin to be pulled upward away from the substrate until the separation distance exceeds the elastic limit of the resin material, causing the material to rupture and form the upper end of the fibril. The point of rupture may be controlled by using a hot wire/hot ribbon 111 placed at the desired distance from the printing roll 110 and the backing roll 108, as is known in the art. In this fashion, control of the point of rupture will generate fibrils of the desired caliper and shape.

With continuing reference to FIG. 3, the process according to the present invention may utilize a variety of types of printing rolls 110 including, but not limited to, a screen printing roll and a Gravure printing roll. In a preferred embodiment of the claimed invention, a screen printing roll is used. A screen printing roll is well known in the art, as illustrated by U.S. Pat. No. 4,628,857, issued to A. Robert Coningsby on Dec. 16, 1986, the disclosure of which is hereby incorporated herein by reference. Gravure printing rolls are also well known in the art as illustrated by U.S. Pat. No. 4,634,130, issued Feb. 17, 1988, to Sheath et al. and incorporated herein by reference to illustrate the general state of the art. A presently preferred print roll comprises a screen with a hexagonal interlocking mesh pattern having an average aperture diameter of 0.035 inches.

If desired, the printing roll 110 may have zones which do not print, hereinafter referred to as non-printing zones. As printing roll 110 preferably comprises a screen printing roll, the screen may have impermeable bars which block transmission of the resinous material through the screen at the positions of the bars. The areas of the printing roll from which resin is applied to the substrate 102 are referred to as the printing zone.

The non-printing zones may be generally longitudinally oriented, parallel to the axis of the printing roll. This arrangement produces generally cross machine direction oriented zones on the substrate 102 which do not contain fibrils. This arrangement may be utilized if desired to trim the resulting web into individual topsheets for disposable absorbent articles with the non-printed areas located at the margins of the absorbent articles, etc.

Alternatively, the non-printing zones may be generally circumferentially oriented, resulting in machine direction oriented zones of the substrate 102 not having the resinous material printed thereon. If desired, several repeating units of the web having zones with and without the resinous material may be juxtaposed together to form a resulting web which is relatively wide in the cross machine direction. The resulting web is then cut in the machine direction at positions corresponding to the desired zones to produce roll stock for use in later production. This arrangement provides the benefits of economy of scale in making disposable absorbent articles.

A doctor blade 112 is used to insure that the resinous material is evenly metered across the entire application face of the printing roll 110. The doctor blade 112 is held stationary as the printing roll 110 is rotated, allowing the doctor blade 112 to wipe the interior surface of the printing roll 110 and force the resinous material into the individual cells of the printing roll 110. The screen of printing roll 110 preferably has a thickness of approximately 4 to 7 millimeters.

The backing roll 108 is smooth and can either comprise a rotatable backing roll (either driven or freely-rotating) or a stationary surface. For the embodiment described herein, the printing roll 110 and the backing roll 108 are maintained in slightly spaced relation so as to avoid unduly compressing the substrate material.

The printing roll 110 is preferably heated to prevent premature solidification of the melted resinous material. A print roll temperature of about 250° F. has been found to work well with the resinous material and process conditions described herein.

While the substrate 102 is preferably comprised of wet laid tissue, any fibrous web that is readily dispersible under mild agitation in cold water is suitable. Suitable materials include, but are not limited to, cotton cellulose and other natural fibers and synthetic fibers, such as polyester, polypropylene, polyethylene, nylon, viscose rayon fibers, cellulose acetate, polyethylene terephthalate, and other natural or synthetic fibers or combinations thereof. The substrate 102 may also be at least partially comprised of chemically modified natural fibers such as cross-linked cellulose fibers. Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,898,642, issued Feb. 6, 1990 to Moore, et al.; U.S. Pat. No. 4,935,022, issued Jun. 6, 1990 to Lash, et al.; U.S. Pat. No. 5,137,537, issued Aug. 11, 1992; and U.S. Pat. No. 5,183,707, issued Feb. 2, 1993 to Herron et al., the disclosures of each of which patents are hereby incorporated herein by reference. Fibrous materials may be carded, hydroentangled, air laid, or wet laid assemblies of hydrophilic fibers.

Suitable cellulosic substrates 102 may be made according to commonly assigned U.S. Pat. Nos. 4,191,609, issued to Paul D. Trokhan or 4,529,480 issued to Paul D. Trokhan, the disclosures of both of which are hereby incorporated herein by reference. A suitable substrate 102 has a basis weight of about 12 pounds per 3000 square feet and is available from Georgia-Pacific Corp. of Bellingham, Wash. under the designation DST-1.

In order to insure easy dispersibility, the fibers of the substrate 102 should either be intrinsically hydrophilic or treated to be hydrophilic. As used therein, a "hydrophilic" material has a contact angle between water and the material surface of less than 90 degrees. Methods of treating fibrous assembles are described in U.S. Pat. No. 4,950,2545, issued to Osborn on Aug. 21, 1994, the disclosure of which is incorporated herein by reference.

A suitable resinous material is a hot melt resin blend that is available from Century International of Columbus, Ohio, under the designation CA-105.

The resinous material may be externally heated by known means (not shown) to maintain the material in a liquid state and at the proper temperature and viscosity. Typically the resinous material is maintained at a temperature slightly above the melting point. The temperature is considered to be at or above the melting point if the resinous material is partially or wholly in the liquid state. If the temperature is too low, it may not transfer from the printing roll 110 to the substrate 102, or subsequently, may not be suitable for printing. Conversely, if the temperature is too high, the material may not be viscous enough to be suitable for the printing process. However, the temperature should not be so high as to damage the substrate 102. For the embodiments described herein, the preferred temperature of the resinous material is from about 190° F. to about 250° F. at the point of application to the substrate 102. This temperature is above the melting point of the aforementioned CA-105 resinous material but below that at which a significant loss of viscoelasticity occurs.

Cooling air may optionally be provided from an air cooling system 114. The cooling air may be necessary to insure that the resinous material already applied to the substrate 102 has solidified before the web is removed from the printing roll 110. Alternatively, backing roll 108 can be chilled to "freeze" the resinous material into the desired fibril configuration. Guide rolls 128 and dancer roll 129 may be utilized to maintain the desired web tension.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fluid pervious, water dispersible and flushable web, said web comprising:
   (a) a cellulosic fibrous substrate, said substrate including a temporary wet strength resin incorporated therein; and
   (b) a plurality of individual fibrils formed from a resinous material affixed to and extending outwardly from a surface of said substrate, said fibrils being spaced at least slightly apart from one another on said surface such that portions of said surface therebetween are at least slightly exposed to provide a fluid pervious, water dispersible and flushable web.

2. The fluid pervious, water dispersible and flushable web of claim 1, wherein said cellulosic fibrous substrate comprises a wetlaid tissue.

3. The fluid pervious, water dispersible and flushable web of claim 1, wherein said substrate includes a plurality of apertures.

4. The fluid pervious, water dispersible and flushable web of claim 1, wherein said fibrils are formed from a water resistant resinous material.

5. The fluid pervious, water dispersible and flushable web of claim 4, wherein said resinous material comprises a silicone resin.

6. The fluid pervious, water dispersible and flushable web of claim 1, wherein said substrate is hydrophilic.

7. The fluid pervious, water dispersible and flushable web of claim 1, wherein said fibrils are hydrophobic.

8. The fluid pervious, water dispersible and flushable web of claim 1, wherein said substrate is hydrophilic and said fibrils are hydrophobic.

9. The fluid pervious, water dispersible and flushable web of claim 1, wherein said fibrils are provided at a density of between about 3000 fibrils per square inch and about 5000 fibrils per square inch.

10. The fluid pervious, water dispersible and flushable web of claim 1, wherein said temporary wet strength resin comprises a glyoxalated polyacrylamide resin.

11. The fluid pervious, water dispersible and flushable web of claim 1, wherein said substrate comprises a wetlaid apertured tissue having between about 20 apertures per square inch and about 111 apertures per square inch.

12. The fluid pervious, water dispersible and flushable web of claim 1, wherein said substrate is free of apertures.

13. The fluid pervious, water dispersible and flushable web of claim 1, wherein said substrate has a varying surface topography.

14. The fluid pervious, water dispersible and flushable web of claim 1, wherein said substrate has a uniform surface topography.

15. The fluid pervious, water dispersible and flushable web of claim 14, wherein said substrate is free of apertures.

16. The fluid pervious, water dispersible and flushable web of claim 1, wherein said substrate comprises a nonwoven material.

17. The fluid pervious, water dispersible and flushable web of claim 1, wherein said fibrils include a masking agent.

18. The fluid pervious, water dispersible and flushable web of claim 1, wherein said fibrils extend outwardly from said surface of said substrate at least about 0.004 inches.

19. A fluid pervious, water dispersible and flushable web, said web comprising:
   (a) a cellulosic fibrous substrate, said substrate including a temporary wet strength resin incorporated therein, said cellulosic substrate comprising a wetlaid tissue, said substrate including a plurality of apertures; and
   (b) a plurality of individual fibrils affixed to and extending outwardly from a surface of said substrate, said fibrils being formed from a water resistant resinous material, said fibrils being spaced at least slightly apart from one another on said surface such that portions of said surface therebetween are at least slightly exposed to provide a fluid pervious, water dispersible and flushable web.

20. A fluid pervious, water dispersible and flushable web, said web comprising:
   (a) a cellulosic fibrous substrate, said substrate including a temporary wet strength resin incorporated therein, said cellulosic substrate comprising a hydrophilic wetlaid tissue, said substrate including a plurality of apertures; and
   (b) a plurality of individual fibrils affixed to and extending outwardly from a surface of said substrate, said fibrils being formed from a hydrophobic water resistant resinous material, said fibrils being spaced at least slightly apart from one another on said surface such that portions of said surface therebetween are at least slightly exposed to provide a fluid pervious, water dispersible and flushable web.

* * * * *